United States Patent [19]
Ishiwatari

[11] Patent Number: 6,013,669
[45] Date of Patent: Jan. 11, 2000

[54] PEST REPELLENT COMPOSITIONS

[75] Inventor: Takao Ishiwatari, Toyonaka, Japan

[73] Assignee: Sumitomo Chemical Company, Limited, Osaka, Japan

[21] Appl. No.: 09/318,274

[22] Filed: May 25, 1999

[30] Foreign Application Priority Data

Jun. 26, 1998 [JP] Japan ................................. 10-180375

[51] Int. Cl.$^7$ ............................ A01N 53/06; A01N 25/34
[52] U.S. Cl. ......................... 514/531; 514/918; 514/919; 514/920; 424/DIG. 10; 424/409
[58] Field of Search ........................... 514/531, 918–920; 424/409, DIG. 10

[56] References Cited

FOREIGN PATENT DOCUMENTS

| | | |
|---|---|---|
| 378026 | 7/1990 | European Pat. Off. . |
| 2225442 | 7/1990 | Japan . |
| 2207605 | 2/1989 | United Kingdom . |

OTHER PUBLICATIONS

Derwent Abstract, Accession No. 1990–218446, Abstracting EP 378,026, 1990.

*Primary Examiner*—John Pak
*Attorney, Agent, or Firm*—Stevens, Davis, Miller & Mosher, L.L.P.

[57] ABSTRACT

The instant invention provides a pest repellent composition that provides an effective repelling of pests by applying said pest repellent composition onto the skin of animals or people, in addition to repelling pests by utilizing said pest repellent compositions in certain locations. As such, the pest repellent compositions of the instant invention comprise 2,3,5,6-tetrafluoro-4-methylbenzyl 3-(2-chloro-2-fluorovinyl)-2,2-dimethylcyclopropanecarboxylate as an active ingredient and an inert carrier. In addition, the instant invention provides methods of repelling pests by utilizing 2,3,5,6-tetrafluoro-4-methylbenzyl 3-(2-chloro-2-fluorovinyl)-2,2-dimethylcyclopropanecarboxylate.

2 Claims, No Drawings

PEST REPELLENT COMPOSITIONS

FIELD OF THE INVENTION

The instant invention relates to pest repellent compositions, and methods of repelling pests.

BACKGROUND OF THE INVENTION

It is well known that N,N-diethyl-m-toluamide (hereinafter referred to as deet) may be utilized in pest repellent compositions, in order to repel blood sucking pests such as mosquitoes, flies, and the like, from people, animals or the like. Such pest repellent compositions comprising deet have been mainly utilized on the skin of animals or people. As a result, recent pest repellent compositions are desired to be more safe (e.g., low toxicity, low stimulation, and the like) when utilized on such skin. Further, the pest repellent compositions comprising deet have additionally been known to fail in providing an effective repelling of blood sucking pests when repelling pests from areas such as residences, warehouses, kitchens, and the like.

SUMMARY OF THE INVENTION

The instant invention provides for pest repellent compositions that can effectively repel pests and a method of repelling pests. In this regard, the pest repellent compositions of the instant invention can repel pests from certain areas which may have pests present therein. Further, the pest repellent compositions of the instant invention can also be utilized on the skin of animals, people, or the like.

Accordingly, the instant invention is able to provide for such advantages by providing pest repellent compositions comprising 2,3,5,6-tetrafluoro-4-methylbenzyl 3-(2-chloro-2-fluorovinyl)-2,2-dimethylcyclopropanecarboxylate as an active ingredient and an inert carrier, as well as a method of repelling pests by utilizing 2,3,5,6-tetrafluoro-4-methylbenzyl 3-(2-chloro-2-fluorovinyl)-2,2-dimethylcyclopropanecarboxylate.

DETAILED DESCRIPTION OF THE INVENTION

A pest repellent composition of the instant invention is typically produced as a formulation comprising 2,3,5,6-tetrafluoro-4-methylbenzyl 3-(2-chloro-2-fluorovinyl)-2,2-dimethylcyclopropanecarboxylate (hereinafter referred to as the instant active compound) as an active ingredient and an inert carrier. In this regard, the pest repellent compositions of the instant invention comprise the instant active compound in an amount that can effectively repel pests, and thereby may comprise the instant active compound in an amount of from about 0.01% to 80% by weight. Further, the instant active compound in the pest repellent compositions of the instant invention may be isomers thereof, provided that the isomers of the instant active compound are active in controlling a pest. Examples of such isomers which may be utilized in the inventive pest repellent compositions as the instant active compound include stereoisomers, i.e. optical or geometrical isomers of the instant active compound or a combination thereof. Especially, 2,3,5,6-tetrafluoro-4-methylbenzyl (1R)-trans-3-(2-chloro-2-fluorovinyl)-2,2-dimethylcyclopropanecarboxylate or isomer mixtures which are enriched of 2,3,5,6-tetrafluoro-4-methylbenzyl (1R)-trans-3-(2-chloro-2-fluorovinyl)-2,2-dimethylcyclopropanecarboxylate are preferably utilized in the instant invention. A method to produce the instant active compound is disclosed in Canadian unexamined Patent Publication 2006835 A.

The inert carriers which are utilized in the pest repellent compositions of the instant invention are typically solid, liquid, or gas carriers, or a mixture thereof.

In addition, the pest repellent compositions may optionally comprise other additives which are known auxiliaries for pesticidal formulations which are utilized for various objects. Examples of such additives that may be utilized in the pest repellent compositions of the instant invention include surfactants, synergists such as N-(2-ethylhexyl)-8,9,10-trinorborn-5-ane-2,3-dicarboxyimide (MGK-264), antioxidents such as butylhydroxyanisole, dibutylhydroxytoluene, tocopherol and γ-oryzanol, UV radiation absorbing agents, coloring agents, pigments and the like, or a mixture thereof.

The pest repellent compositions of the instant invention are usually produced into formulations which allow the instant active compound therein to be active to repel pests. Accordingly, the pest repellent compositions of the instant invention are usually produced by incorporating the instant active compound and an inert carrier, or a mixture comprising the instant active compound and an inert carrier. The pest repellent compositions may also be produced by adding the optional additives such as the surfactants and other formulation auxiliaries which are useful in producing the inventive pest repellent compositions to the instant active compound. Examples of formulations of the inventive pest repellent composition include formulations in a sheet form, formulations in which the instant active compound is kneaded into a resin or resins, emulsifiable concentrates, oil formulations, wettable powders, flowables of aqueous suspensions or aqueous emulsions, granules, powders, aerosols, incenses, electric mosquito mat formulations, formulations in which the instant active compound is absorbed into a liquid-absorbing wick so that the instant active compound can be electrically heat vaporized, microcapsules, gel paste formulations, and the like.

A method of the instant invention repels pests by utilizing the inventive pest repellent compound. In this regard, the methods of the instant invention typically repel pests by applying, distributing, spraying, spreading or setting the pest repellent compound in an appropriate location. Further, the methods of the instant invention typically utilize the pest repellent compositions in an amount that is dependent on the formulation of the pest repellent compositions and/or the objective pest which said pest repellent compositions are attempting to repel. For example, provided that a pest repellent composition is utilized on a wall surface, flooring surface, land surface, or the like, or a combination thereof, a method of the instant invention should utilize 0.01 g to 10 g of the instant active compound per every square meter of the location in which the provided pest repellent composition is attempting to repel pests.

When the pest repellent compositions are employed in the methods of the instant invention, locations of where said pest repellent compositions should be utilized typically include the skin of animals (e.g., cats, dogs, hamsters, cows, bulls, rabbits, horses, pigs, lambs, and other domestic animals) or people, or areas in which pests invade or are otherwise present. Examples of such areas that are vulnerable to an invasion of pests and in which the methods of the instant invention utilizes the inventive pest repellent compositions, include rooms of a residence, wall or floor regions of kitchens or warehouses, utensils, curtains, screen doors, and the like. In addition, the methods of the instant invention may repel pests by utilizing the inventive pest repellent compositions in an area which is in the whereabouts between said areas which are vulnerable to an invasion of pests and the exteriors thereof, with examples of such areas including windows; doors; the entrance or exit of rooms, kitchens or warehouses; and the like, or a combination thereof. Even if so, it should be noted that the instant invention is not limited to a method of repelling pests in such specific locations, since it is well known that pests may invade or be present in additional locations where the pest repellent compositions and methods of the instant invention would be applicable.

For example, a method of the instant invention may utilize the instant active compound by applying the instant active compound, preferably a cream or liquid formulation of the instant active compound, onto the skin of animals or people, when repelling blood sucking pests such as mosquitoes, black flies, stable flies, and the like. Similarly, one of the methods of the instant invention may utilize the instant active compound by producing household utensils which comprise the instant active compound. In such a method of the instant invention, the household utensil is typically produced by previously spreading, soaking, kneading or dripping the instant active compound into the components of the utensil, such as woods, resins, or the like, and then formed into the desired household utensil. Thereafter, such a method should utilize the achieved household utensil comprising the inventive pest repellent composition in an appropriate location. If so desired, a method of the instant invention may also repel pests by heating an appropriate formulation of the instant active compound in an appropriate location.

In this regard, pests which are repelled by utilizing the pest repellent compositions of the instant invention typically include blood sucking pests, pests of foods or other edible products, noxious pests, or the like. More specifically, examples of such pests which are repelled by the inventive pest repellent compositions include Diptera, for example, Anopheles spp., Aedes spp. such as yellow fever mosquito, (*Aedes aegypti*) and *Aedes albopictus*, Culex spp. such as common house mosquito (*Culex pipiens pallens*) and *Culex tritaeniorhynchus*, black flies (Simuliidae), stable flies (Stomoxyidae), sand flies, biting midges (Ceratopogonidae), house flies (Muscidae), vinegar flies (Drosophilidae), moth flies, and the like are suitable. Other than that, a repelling of the pests of Dictoptera such as German cockroach (*Blattella germanica*), smokybrown cockroach (*Periplaneta fuliginosa*), American cockroach (*Periplaneta americana*), brown cockroach (*Periplaneta brunnea*) and oriental cockroach (*Blatta orientalis*); Coleoptera such as maize weevil (*Sitophilus zeamais*), adzuki bean weevil (*Callosobruchus chinensis*), red flour beetle (*Tribolium castaneum*), black carpet beetle (*Attagenus unicolor japonicus*), varied carpet beetle (*Authrenus verbasci*), deathwatch beetles (Anobiidae), powderpost beetles (Lyctidae) and robe beetle (Paederus fuscipes); Hymenoptera such as ants (Formicidae) and Bethylidae; Siphonaptera such as fleas (Pulicidae); lice (Anoplura) such as *Pediculus humanus* and crab louse (*Pthirus pubis*); termites (Isoptera) such as *Reticulitermes speratus* and Formosan subterranean termite (*Coptotermes formosanus*); house dust mites such as Acaridae, Pyroglyphidae and Cheyletidae; Ixodidae such as the *Boophilus microplus; Ornithonyssus bacoti*, and the like is also possible by using the instant active compound.

If necessary, the pest repellent compositions may also repel or retard aphids (Aphididae) from sucking juices, and thereby abstain the aphids from spreading contagious botanical diseases, wherein said aphids serve as a vector for a virus of botanical diseases.

Optionally, the pest repellent compositions of the instant invention may contain other well known pest repelling or pesticidal compounds to repel or control additional pests. Exemplarily of the other pest repelling compounds which may be in the inventive pest repellent compositions, caranc-3,4-diol, deet, p-menthane-3,8-diol, 2,3,4,5-bis($\Delta$2-butylene)tetrahydrofurfural, di-n-propylisocinchomeronate, di-n-butylsuccinate, 2-hydroxyoctylsulfide, (N-carbo-sec-butyloxy)-2-(2-hydroxyethyl)piperidine, hyssop oil, and the like, or a mixture thereof. Examples of the pesticidal compounds which may be utilized in the pest repellent compositions of the instant invention include empenthrin, transfluthrin, prallethrin, tetramethrin, phenothrin, cyphemothrin, permethrin, cypermethrin, cyhalothrin, resmethrin, cyfluthrin, fenvalerate, deltamethrin, tralomethrin, tefluthrin, etofenprox, silafluofen, furamethrin, imiprothrin, terallethrin, methoxydiazone, propoxur, fenitrothion, dichlorvos, and the like, or a mixture thereof.

EXAMPLES

Hereinafter, the instant invention is explained in further detail by the examples, but the instant invention is not limited thereto.

Formulation Example 1

One milligram (1 mg) of 2,3,5,6-tetrafluoro-4-methylbenzyl (1R)-trans-3-(2-chloro-2-fluorovinyl)-2,2-dimethylcyclopropane carboxylate (hereinafter, referred to as the 1R trans compound) is dissolved in an appropriate amount of acetone, to obtain a mixture. The obtained mixture is spread onto a 2 cm×2 cm filter paper possessing a thickness of 0.3 mm, and is then allowed to dry, so that a pest repellent sheet can be obtained.

Formulation Example 2

One (1) part by weight of the 1R trans compound is dissolved in 49 parts by weight of ethanol, and the achieved solution is packed into an aerosol container. After a valve is affixed to the aerosol container, 50 parts by weight of LPG is compressed under pressure, and through the valve to obtain an aerosol of the 1R trans compound.

Formulation Example 3

One (1) part by weight of the 1R trans compound, 10 parts by weight of stearic acid, 2 parts by weight of cetyl alcohol, 1 part by weight of lanolin, 2 parts by weight of liquid paraffin and 71 parts by weight of water are incorporated, heated, and dissolved and mixed, to achieve a mixture. Thirteen (13) parts by weight of heated glycerin is then poured into the achieved mixture so that the cream formulation of the 1R trans compound is obtained.

Formulation Example 4

A mixture of 6 parts by weight of stearic acid, 0.5 parts by weight of lanolin and 6 parts by weight polyoxyethylene-sorbitan monostearate is heated to 80° C., and then added to a second mixture of 84 parts by weight of water and 2.5 parts by weight of salicylic acid which is at 60° C. Subsequently, while the achieved mixture is stirred at a high speed, 1 part by weight of the 1R trans compound is added to the stirred mixture, so that the lotion formulation of the 1R trans compound is obtained.

Test Example

An entrance for mosquitoes was cut out of a plastic cup having a 10 cm diameter at the closed end (or bottom) of the cup, a 12 cm diameter at the open end (or top) of the cup, a height of 7 cm and a volume of 650 mL, by cutting a 2 cm×2 cm section out of the closed-end portion of the side of the cup. A mosquito attractant was then prepared by folding a 13.5 cm×10 cm disposable hand warmer (Kiribai NEW hand warmer 24 hour type) in half and then placing the folded hand warmer within said cup. A pest repellent sheet of Formulation Example 1 was affixed to a surface of a cover by using a double sidled adhesive tape. The cover was then placed onto the cup so that the surface containing the said pest repellent sheet faced the inside of the cup. Thereafter, the pest repellent sheet was allowed to vaporize in the cup for a duration of 1 minute.

In a 50 cm×50 cm×50 cm nylon gauze cage containing about 600 yellow fever mosquitoes (*Aedes aegypti*) which had a male to female ratio of about 1:1, 2 prepared cups were position in opposing corners therein and which at a position of about 10 cm from each according corner of the cage, in order to attract said mosquitoes. After the prepared cups were allowed to attract said mosquitoes in the cage for about 10 minutes, the cups were removed and then number of female mosquitoes attracted into the cup were examined.

A control was performed by a similar method, but a filter paper which did not contain the 1R trans compound was utilized as a pest repellent sheet instead of the pest repellent sheet of Formulation Example 1.

Comparative tests were also performed by a similar method, but a pest repellent sheet containing Compound A, Compound B, or Compound C, which are encompassed by the following general formulas:

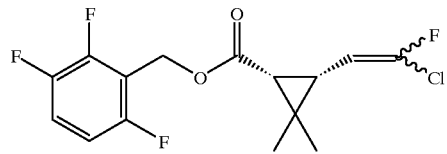
Compound A

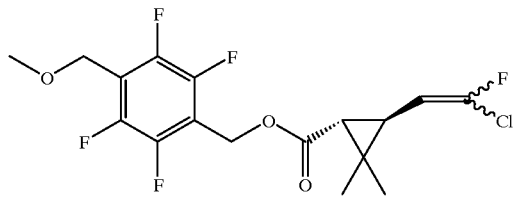
Compound B

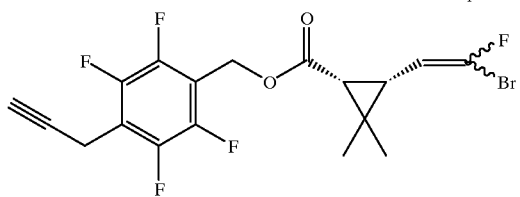
Compound C were utilized instead of the pest repellent sheet of Formulation Example 1.

The repelling rate of each compound was then calculated by applying the achieved results of each compound and the control into the following equation:

Repelling Rate $100 \times [(Q-P)/Q]$ wherein "P" represents the number of pests attracted into the cup which contained either the 1R trans compound, Compound A, Compound B, or Compound C, and "Q" represents the number of pests attracted into the cup of the control (in which the cup contained no compound). The test results are set forth in Table 1.

TABLE 1

| Utilized Composition | Applied Amount (mg/filter paper) | Repelling Rate (%) |
| --- | --- | --- |
| 1R trans Compound | 1 | 82 |
| Compound A | 1 | 41 |
| Compound B | 1 | 45 |
| Compound C | 1 | 7 |

The above test results evidence that the pest repelling compositions of the instant invention provide an advantageous pest repelling activity, and that analogs of the instant active compound would not result in such advantageous results.

What is claimed is:

1. A method of repelling pests comprising applying an effective amount of 2,3,5,6-tetrafluoro-4-methylbenzyl 3-(2-chloro-2-fluorovinyl)-2,2-dimethylcyclopropanecarboxylate to people, animals, or locus where the pests invade.

2. The method according to claim 1, wherein the pests are mosquitoes.

* * * * *

UNITED STATES PATENT AND TRADEMARK OFFICE
CERTIFICATE OF CORRRECTION

PATENT NO. : 6,013,669
DATED : January 11, 2000
INVENTOR(S) : Takao Ishiwatari It is certified that error appears in the above-identified patent and that said Letters Patent is hereby corrected as shown below:

On the title page, item [56] insert the following:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 6 | 3 | 2 | 8 | 4 | 3 | A | 10/96 | WO | | | | |
| | | 0 | 0 | 3 | 1 | 1 | 9 | 9 | A | 07/81 | EP | | | | |

OTHER DOCUMENTS(Including Author, Title, Date, Pertinent Pages, Etc.)

European Search Report dated December 6, 1999

Signed and Sealed this

Twenty-seventh Day of June, 2000

Attest:

Q. TODD DICKINSON

*Attesting Officer*   *Director of Patents and Trademarks*